US006471971B1

(12) United States Patent
Wollenweber et al.

(10) Patent No.: US 6,471,971 B1
(45) Date of Patent: Oct. 29, 2002

(54) CELLULOSE-ETHER-STABILIZED OIL-IN-WATER EMULSIONS AS A VEHICLE FOR HOMEOPATHIC AND HERBAL ACTIVE INGREDIENTS

(75) Inventors: Christian Wollenweber, Karlsruhe (DE); Rainer Oschmann, Landau (DE); Marianne Heger, St. Leon-Rot (DE); Rolf Daniels, Salzgitter (DE)

(73) Assignee: Deutsche Homoeopathic-Union, Karlsruhe (DE)

( * ) Notice: Subject to any disclaimer, the term of this patent is extended or adjusted under 35 U.S.C. 154(b) by 0 days.

(21) Appl. No.: 09/695,938

(22) Filed: Oct. 25, 2000

(30) Foreign Application Priority Data

Oct. 26, 1999 (DE) .......................................... 199 51 474

(51) Int. Cl.[7] .............................. A61K 7/00; A61K 7/48
(52) U.S. Cl. ........................ 424/400; 424/401; 424/59; 424/70.6
(58) Field of Search ......................... 424/401, 59, 70.6, 424/400, 450; 435/41

(56) References Cited

U.S. PATENT DOCUMENTS 5,466,443 A * 11/1995 Ho et al. .................... 424/70.6
6,046,022 A * 11/1997 Zhang et al. ................... 435/41
6,074,652 A * 1/1998 Ishiwatari et al. ........... 424/401
5,804,168 A * 9/1998 Murad ......................... 424/59

FOREIGN PATENT DOCUMENTS

JP         WO 9940887           *    8/1999

OTHER PUBLICATIONS

Rimpler S. and R. Daniels, "Effect of oil content on the properties of emulsions containing HPMC as polymeric emulsifier," Proc. 1st World Meeting APGI/APV, Budapest, 9/11, May. 651–652, (1995).
Ashton P., et al., "Effects of surfactants in percutaneous adsorption," pharm. Acta Helv. 61 (8), 228–235, 1986.
Barta A. and Daniels R., "Pharmacopoeial cellulose ethers as o/w emulsifiers—I. Interfacial properties," Eur. J. Pharm. Biopharm., 40, 128–133. (1994).

* cited by examiner

Primary Examiner—Jose' G. Dees
Assistant Examiner—Mina Haghighatian
(74) Attorney, Agent, or Firm—Davidson, Davidson & Kappel, LLC

(57) ABSTRACT

An oil-in-water emulsion preparation comprises oil, water, alcohol, at least one of an homeopathic active ingredient and an herbal active ingredient, and a cellulose ether. A method of preparing an emulsion and a use of the emulsion are also provided.

19 Claims, No Drawings

CELLULOSE-ETHER-STABILIZED OIL-IN-WATER EMULSIONS AS A VEHICLE FOR HOMEOPATHIC AND HERBAL ACTIVE INGREDIENTS

BACKGROUND OF THE INVENTION

1. Field of the Invention

The present invention concerns an oil-in-water emulsion preparation containing alcoholic, homeopathic and/or herbal active ingredients.

2. Background Information

Preparations applied to the skin (dermatics) with homeopathic or herbal active ingredients are distinguished in that they only contain a few adjuvants that are natural in origin. No stabilizers, antioxidants and preservatives should be used. The creation and composition of such preparations are described in detail in the Homeopathic Pharmacopoeia (HAB). For example in regard to ointments, it prescribes (according to specification 13) that water-containing wool-wax alcohol ointment as per the German pharmacopoeia (DAB) is to be used as a base, i.e., a vehicle for the active ingredient(s). If other bases are used, they must be stated. The homeopathic active ingredient(s) are incorporated into the base. Such water-in-oil or oil-in-water emulsion preparations, termed "W/O" and "O/W emulsion preparations" in the following are frequently physically instable when the homeopathic active ingredients are added in the form of mother tinctures and/or dilutions due to the alcohol content (especially ethanol content) of the mother tinctures/dilutions. There hence exists a need for other preparations that have a sufficiently high alcohol and especially ethanol tolerance and are permitted by the HAB.

Normally, emulsifiers are used to stabilize O/W emulsion preparations. These usually low-molecular substances can interact with the skin due to their amphiphile structure [Ashton P., et al., "Effects of surfactants in percutaneous adsorption," pharm. Acta Helv. 61 (8), 228–235, 1986] and hence generate incompatibility reactions such as toxic-irritating reactions or contact allergies.

State-of-the-art suitable adjuvants for stabilizing certain specific emulsions are in particular cellulose ethers, so-called polymer emulsifiers. They are suitable for stabilizing these certain emulsions since they are adsorbed at O/W interfaces, lower the interface tension between the outer and inner phase, and form stabile interface films [Barta A. and Daniels R., "Pharmacopoeial cellulose ethers as o/w emulsifiers—I. Interfacial properties," Eur. J. Pharm. Biopharm., 40, 128–133. (1994)]. Cellulose ethers enjoy widespread use as adjuvants in certain pharmacy and foods technology. In solid drug forms, they are used as a binder for granules, a matrix former for the delayed release of active ingredients, and as a film former that is dissolved by stomach and intestinal juices. In liquid preparations, they primarily serve to increase viscosity of eye drops; at higher concentrations, they also serve as a hydrogel former. It has been determined that cellulose-ether-containing preparations are well-tolerated in eyes. There are no known undesirable side-effects on the skin for this class of substances.

The use of various cellulose ethers to stabilize alcohol-free O/W emulsions has been investigated in recent years where particularly positive results were obtained with hypromellose-stabilized O/W emulsions that contain medium-chain triglycerides as an oil phase [Rimpler S. and R. Daniels, "Effect of oil content on the properties of emulsions containing HPMC as polymeric emulsifier," Proc. 1st World Meeting APGI/APV, Budapest, 9/11 May 651–652, (1995)].

In addition to the problem of satisfactory stabilization, another problem with O/W emulsion preparations is that water-containing preparations tend to be susceptible to microbial attack. Germs can be introduced during manufacture and during use by the patient. The use of preservatives in such preparations is therefore appropriate, but preservatives can trigger incompatibility reactions in patients and are preferably avoided for this reason.

SUMMARY OF THE INVENTION

An object of the present invention is to present well-tolerated and sufficiently preserved emulsion preparations as a base for homeopathic mother tinctures and dilutions, liquid plant extracts and ethanolic tinctures. The vehicles should have very few adjuvants that are preferably described in the pharmacopoeias (Pharmacopoia Europa (Ph Eur), German Pharmacopoeia (DAB), Homeopathic Pharmacopoeia (HAB), United States Pharmacopoeia (USP)) in a monograph and are hence judged harmless; it should be easy to prepare and incorporate the active ingredient(s) in a laboratory and on a mass-production scale.

The present invention provides an O/W emulsion preparation containing an alcohol and an homeopathic and/or other herbal active ingredient, the preparation being characterized in that it contains cellulose ether as an additive.

The cellulose-ether-stabilized, oil-in-water emulsion preparations containing active ingredient in alcohol (i.e.: containing alcohol and homeopathic and herbal active ingredient(s)) are distinguished primarily in that they are surprisingly very stable in storage. This storage stability is clearly greater than would be expected based on state-of-the-art professional knowledge on hypromellose-stabilized emulsions. The present invention is based on the surprising insight that adding alcohol and especially ethanol substantially improves the storage stability of hypromellose-stabilized emulsions. This insight contrasts with the predominant opinion of the professional world up to now that asserts that O/W emulsions become unstable with the addition of alcohol-containing liquids such as liquid homeopathic tinctures and dilutions, or plant extracts in alcohol.

In addition, the O/W emulsion preparations according to the present invention have the advantage that the emulsion is sufficiently preserved, and other preservatives do not need to be added at a correspondingly high alcohol concentration (especially ethanol concentration) of e.g. 15 mass percent (% m/m).

Another advantage of the O/W emulsion preparations according to the present invention is that they are substantially easier to prepare in contrast to conventional alcohol-free and ethanol-free emulsions; the polymer emulsifiers can disperse without being heated to high temperatures by adding alcohol-containing or ethanol-containing active ingredient to the preparation and/or the adding pure ethanol.

The problem on which the present invention is based is also solved by the presentation of a procedure to create a cellulose-ether-containing O/W emulsion preparation containing homeopathic and/or herbal active ingredients in alcohol that is characterized by the number and series of the procedural steps below:

1. The cellulose ether(s) is/are dissolved in the alcoholic-aqueous emulsion phase, and
2. The cellulose-ether-containing alcoholic-aqueous emulsion phase obtained in this manner is then homogenized with the oil (oil phase).

This preparation procedure according to the present invention has advantages over conventional procedures: It is much faster since only two procedural steps are required whereas the conventional procedure has four steps, and less energy must be expended because the emulsion no longer has to be heated to disperse the polymer emulsifier.

The following cellulose ethers, by themselves or together and preferably in an amount of 0.1 to 10 mass percent (in reference to the overall mass of the emulsion preparation), that are used to prepare the cellulose-ether-stabilized, active-ingredient-containing emulsion preparations according to the present invention are preferably:

Methylcellulose Ph Eur

Hydroxypropylcellulose Ph Eur

Hypromellose (syn Methylhydroxypropylcellulose) Ph Eur

Methylhydroxyethylcellulose Ph Eur

Hydroxyethylcellulose Ph Eur

Sodium carboxymethylcellulose Ph Eur.

Suitable dispersed phases of the O/W emulsion preparations according to the present invention are in particular the following oils, individually or together, and preferably in an amount of 1 to 74 mass percent (in reference to the overall mass of the emulsion preparation):

Medium-chain triglycerides Ph Eur

Peanut oil Ph Eur

Castor oil Ph Eur

Highly liquid paraffin Ph Eur

Highly viscous paraffin Ph Eur.

Suitable active ingredients of the emulsion preparations according to the present invention are homeopathic mother tinctures and dilutions, liquid alcoholic plant extracts and other alcoholic and especially ethanolic tinctures. They are preferably used in an amount of 1 to 50 mass percent (in reference to the overall mass of the emulsion preparation).

To further increase the storage stability and resistance to microbial attack, the emulsion preparations according to the invention can have ethanol, preferably in an amount of 1 to 20 mass percent (in reference to the overall mass of the emulsion preparation) in addition to the alcoholic active ingredients.

All the emulsion preparations according to the present invention are quite suitable for preparing homeopathic and/or phytopharmaceutic drugs. The present invention therefore also concerns homeopathic and/or herbal drugs that have been prepared using an emulsion preparation according to the present invention.

The present invention will be further explained in the following with reference to exemplary embodiments:

EXAMPLE 1

Comparison of the Preparation of (Conventional) Ethanol-free O/W Emulsions (Conventional) and Ethanol-containing O/W Emulsions (According to the Present Invention)

(A) Ethanol-free Hypromellose-stabilized O/W Emulsions (Hot Preparation, Conventional Procedure According to the State-of-the-art)

1. Hypromellose is dispersed in hot water (90° C.). The suspension is cooled to room temperature while being stirred. A clear, opalescent solution arises. Evaporated water is replenished.
2. The alcohol-free mother tincture (or extract) is added to the hypromellose solution while being stirred until a homogenous solution arises.
3. The aqueous phase and oil phase are heated to 40° C.
4. The oil phase is worked into the aqueous phase. The phases are homogenized with a rotor-stator homogenizer. A homogenous emulsion arises.

(B) Ethanol-containing Hypromellose-stabilized O/W Emulsions (Cold Preparation, Procedure According to the Present Invention)

1. Hypromellose is made into a paste with ethanol. Water and mother tincture (or extract) are added to the hypromellose suspension under agitation to form a homogenous solution (aqueous phase).
2. The oil phase is worked into the aqueous phase. The phases are homogenized with a rotor-stator homogenizer. A homogenous emulsion arises.

EXAMPLE 2

Recipe of a Cellulose-ether-stabilized Homeopathic, Mother-tincture-containing O/W Emulsion According to the Invention Contents:

| | |
|---|---|
| Hypromellose Ph Eur | 1.0% m/m |
| Cardiospermum halicacabum HAB | 10.0% m/m |
| Ethanol Ph Eur | 8.0% m/m |
| Medium-chain triglycerides Ph Eur | 10.0% m/m |
| Purified water Ph Eur | add to 100.0% m/m |

Preparation:

1. A paste is formed from hypromellose and ethanol. Water and Cardiospermum halicacabum mother tincture (or extract) are added to this hypromellose suspension under agitation to form a homogenous solution (aqueous phase).
2. The medium-chain triglycerides (oil phase) are worked into the aqueous phase, and this mixture is homogenized with a rotor-stator homogenizer.

EXAMPLE 3

Recipe of a Cellulose-ether-stabilized O/W Emulsion According to the Present Invention Containing Arnica Tincture Contents:

| | |
|---|---|
| Hypromellose Ph Eur | 2.0% m/m |
| Arnica tincture DAB | 50.0% m/m |
| Ethanol Ph Eur | 5.0% m/m |
| Medium-chain Triglyceride Ph Eur | 5.0% m/m |
| Purified water Ph Eur | add to 100.0% m/m |

Preparation:

1. A paste is formed with hypromellose and ethanol. Water and arnica mother tincture (or extract) are added to this hypromellose suspension under agitation to form a homogenous solution (aqueous phase).
2. The middle-chain triglycerides (oil phase) are worked into the aqueous phase, and this mixture is homogenized with a rotor-stator homogenizer.

EXAMPLE 4

Recipe of a Second Cellulose-ether-stabilized O/W
Emulsion According to the Present Invention
Containing *Cardiospermum halicacabum*

Contents:

| | |
|---|---|
| Sodium carboxymethylcellulose Ph Eur | 3.0% m/m |
| Cardiospermum halicacabum HAB | 30.0% m/m |
| Ethanol Ph Eur | 5.0% m/m |
| Highly liquid paraffin Ph Eur | 20.0% m/m |
| Purified water Ph Eur | add to 100.0% m/m |

Preparation:
1. A paste is formed with sodium carboxymethylcellulose and ethanol. Water and Cardiospermum halicacabum mother tincture (or extract) are added to this sodium carboxymethylcellulose suspension under agitation, and a homogenous solution (aqueous phase) is formed.
2. The highly-liquid paraffin (oil phase) is worked into the aqueous phase, and this mixture is homogenized with a rotor-stator homogenizer.

EXAMPLE 5

Recipe of a Cellulose-ether-stabilized O/W
Emulsion According to the Present Invention
Containing Hamamelis Mother Tincture Contents:

| | |
|---|---|
| Hypromellose Ph Eur | 2.0% m/m |
| Hamamelis HAB | 20.0% m/m |
| Ethanol Ph Eur | 5.0% m/m |
| Medium-chain triglycerides Ph Eur | 20.0% m/m |
| Purified water Ph Eur | add to 100.0% m/m |

Preparation:
1. A paste is formed with hypromellose and ethanol. Water and Hamamelis mother tincture are added to this hypromellose suspension under agitation to form a homogenous solution (aqueous phase).
2. The medium-chain triglycerides (oil phase) are worked into the aqueous phase, and this mixture is homogenized with a rotor-stator homogenizer.

EXAMPLE 6

Recipe of a Cellulose-ether-stabilized O/W
Emulsion According to the Present Invention
Containing Calendula Mother Tincture Contents:

| | |
|---|---|
| Hypromellose Ph Eur | 2.0% m/m |
| Calendula HAB | 10.0% m/m |
| Ethanol Ph Eur | 8.0% m/m |
| Medium-chain triglycerides Ph Eur | 20.0% m/m |
| Purified water Ph Eur | add to 100.0% m/m |

Preparation:
1. A paste is formed with hypromellose and ethanol. Water and Calendula mother tincture are added to this hypromellose suspension under agitation to form a homogenous solution (aqueous phase).
2. The medium-chain triglycerides (oil phase) are worked into the aqueous phase, and this mixture is homogenized with a rotor-stator homogenizer.

EXAMPLE 7

Recipe of a Cellulose-ether-stabilized O/W
Emulsion According to the Present Invention
Containing Berberis Mother Tincture Contents:

| | |
|---|---|
| Hypromellose Ph Eur | 2.0% m/m |
| Berberis HAB | 5.0% m/m |
| Ethanol Ph Eur | 10.0% m/m |
| Medium-chain triglycerides Ph Eur | 20.0% m/m |
| Purified water Ph Eur | add to 100.0% m/m |

Preparation:
1. A paste is formed from hypromellose and ethanol. Water and Berberis mother tincture are added to this hypromellose suspension under agitation to form a homogenous solution (aqueous phase).
2. The medium-chain triglycerides (oil phase) are worked into the aqueous phase, and this mixture is homogenized with a rotor-stator homogenizer.

EXAMPLE 8

Recipe of a Cellulose-ether-stabilized O/W
Emulsion According to the Present Invention
Containing Cardiospermum Mother Tincture Contents:

| | |
|---|---|
| Hypromellose Ph Eur | 10.0% m/m |
| Cardiospermum HAB | 10.0% m/m |
| Ethanol Ph Eur | 8.0% m/m |
| Medium-chain triglycerides Ph Eur | 30.0% m/m |
| Purified water Ph Eur | add to 100.0% m/m |

Preparation:
1. A paste is formed from hypromellose and ethanol. Water and Cardiospermum mother tincture are added to this hypromellose suspension under agitation to form a homogenous solution (aqueous phase).
2. The medium-chain triglycerides (oil phase) are worked into the aqueous phase, and this mixture is homogenized with a rotor-stator homogenizer.

EXAMPLE 9

Recipe of a Cellulose-ether-stabilized O/W
Emulsion According to the Present Invention
Containing Cardiospermum Mother Tincture Contents:

| | |
|---|---|
| Hypromellose Ph Eur | 5.0% m/m |
| Cardiospermum HAB | 5.0% m/m |
| Ethanol Ph Eur | 20.0% m/m |
| Medium-chain triglycerides Ph Eur | 40.0% m/m |
| Purified water Ph Eur | add to 100.0% m/m |

Preparation:
1. A paste is formed from hypromellose and ethanol. Water and Cardiospermum mother tincture are added to this hypromellose suspension under agitation to form a homogenous solution (aqueous phase).
2. The medium-chain triglycerides (oil phase) are worked into the aqueous phase, and this mixture is homogenized with a rotor-stator homogenizer.

EXAMPLE 10

Recipe of a Cellulose-ether-stabilized O/W Emulsion According to the Present Invention Containing Cardiospermum Mother Tincture Contents:

| | |
|---|---:|
| Hypromellose Ph Eur | 1.0% m/m |
| Cardiospermum HAB | 10.0% m/m |
| Ethanol Ph Eur | 8.0% m/m |
| Medium-chain triglycerides Ph Eur | 60.0% m/m |
| Purified water Ph Eur | add to 100.0% m/m |

Preparation:
1. A paste is formed from hypromellose and ethanol. Water and Cardiospermum mother tincture are added to this hypromellose suspension under agitation to form a homogenous solution (aqueous phase).
2. The medium-chain triglycerides (oil phase) are worked into the aqueous phase, and this mixture is homogenized with a rotor-stator homogenizer.

What is claimed is:

1. An oil-in-water emulsion preparation consisting of:
   oil;
   water;
   alcohol;
   at least one of an homeopathic or herbal active ingredient; and
   a cellulose ether.

2. The oil-in-water emulsion preparation according to claim 1, wherein the cellulose ether is 0.1–10 mass percent of the preparation.

3. The oil-in-water emulsion preparation according to claim 1, wherein the alcohol and the at least one homeopathic and herbal active ingredient are 1–50 mass percent of the preparation.

4. The oil-in-water emulsion preparation according to claim 1, wherein the oil is 1–74 mass percent of the preparation.

5. The oil-in-water emulsion preparation according to claim 1, wherein in the cellulose ether includes hypromellose or methylhydroxypropylcellulose individually or together with other cellulose ethers.

6. The oil-in-water emulsion preparation according to claim 1, wherein the cellulose ether includes hydroxypropylcellulose individually or together with other cellulose ethers.

7. The oil-in-water emulsion preparation according to claim 1, wherein the cellulose ether includes methylcellulose individually or together with other cellulose ethers.

8. The oil-in-water emulsion preparation according to claim 1, wherein the cellulose ether includes at least one of methylhydroxyethylcellulose, hydroxyethylcellulose and sodium carboxymethylcellulose.

9. The oil-in-water emulsion preparation according to claim 1 wherein the oil includes triglycerides.

10. The oil-in-water emulsion preparation according to claim 1, wherein the oil includes peanut oil.

11. The oil-in-water emulsion preparation according to claim 1, wherein the oil includes castor oil.

12. The oil-in-water emulsion preparation according to claim 1, wherein the oil includes highly-liquid paraffin.

13. The oil-in-water emulsion preparation according to claim 1, wherein the oil includes highly-viscous paraffin.

14. The oil-in-water emulsion preparation according to claim 1 wherein the alcohol is ethanol comprising 1–20 mass percent of the preparation.

15. The oil-in-water emulsion preparation according to claim 1 wherein the alcohol is ethanol.

16. The oil-in-water emulsion preparation according to claim 1 wherein the at least one homeopathic active ingredient and herbal active ingredient is predissolved in the alcohol.

17. A method for preparing a cellulose-ether-stabilized oil-in-water emulsion comprising the steps of:
   first dissolving a cellulose ether in an alcoholic-aqueous emulsion phase using solely the cellulose ether as the emulsifier; and
   homogenizing the cellulose-containing, alcoholic emulsion phase with an oil phase.

18. A method for preparing homeopathic or herbal drugs comprising the step of combining solely oil, water, alcohol, at least one of an homeopathic or herbal active ingredient, and cellulose ether.

19. The method as recited in claim 17 wherein all of the steps occur at room temperature.

* * * * *

UNITED STATES PATENT AND TRADEMARK OFFICE
CERTIFICATE OF CORRECTION

| | | |
|---|---|---|
| PATENT NO. | : 6,471,971 B1 | Page 1 of 1 |
| DATED | : October 29, 2002 | |
| INVENTOR(S) | : Christian Wollenweber, Rainer Oschmann, Marianne Heger and Rolf Daniels | |

It is certified that error appears in the above-identified patent and that said Letters Patent is hereby corrected as shown below:

<u>Title page,</u>
Item [73], should read -- Assignee: Dr. Wilmar Schwabe Gmbh & Co., Karlsruhe --

Signed and Sealed this

Thirteenth Day of May, 2003

JAMES E. ROGAN
*Director of the United States Patent and Trademark Office*